(12) United States Patent
Randall et al.

(10) Patent No.: US 8,148,159 B2
(45) Date of Patent: Apr. 3, 2012

(54) SYSTEM AND METHODS FOR STRETCHING POLYNUCLEOTIDES

(75) Inventors: Greg Randall, Methuen, MA (US); Patrick Doyle, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 434 days.

(21) Appl. No.: 11/868,174

(22) Filed: Oct. 5, 2007

(65) Prior Publication Data
US 2008/0213912 A1 Sep. 4, 2008

Related U.S. Application Data

(60) Provisional application No. 60/849,582, filed on Oct. 5, 2006.

(51) Int. Cl.
*G01N 33/58* (2006.01)
*B01J 19/00* (2006.01)

(52) U.S. Cl. ....... 436/94; 430/322; 422/82.05; 422/243; 204/600

(58) Field of Classification Search ........ 436/94; 430/322; 422/82.05, 243; 204/600
See application file for complete search history.

(56) References Cited

U.S. PATENT DOCUMENTS
2005/0196702 A1* 9/2005 Bryant et al. ............. 430/311
2007/0111303 A1* 5/2007 Inoue et al. ............. 435/287.2

OTHER PUBLICATIONS

Chan et al.(2004). DNA Mapping Using Microfluidic Stretching and Single-Molecule Detection of Fluorescent Site-Specifica Tags. Genome Research 14:1137-1146.*

Dimalanta, et al., "A Microfluidic System for Large DNA Molecule Arrays", Anal Chem, 76: 5293-5301, 2004.
Ferree, et al., "Electrokinetic Stretching of Tethered DNA", Biophysical Journal, 85: 2539-2546, 2003.
Kaji, et al., "Stretching of megabase-sized deoxyribonucleic acid molecules by tuning electric-field frequency", Applied Physics Letters, 83: 3413-3415, 2003.
Larson, et al., "Single DNA molecule stretching in sudden mixed shear and elongational microflows", Lab Chip, 6: 1187-1199, 2006.
Perkins, et al., "Stretching of a Single Tethered Polymer in a Uniform Flow", Science, 268: 83-87, 1995.
Petit, et al., "Combing of Molecules in Microchannels (COMMIC): A Method for Micropatterning and Orienting Stretched Molecules of DNA on a Surface", Nano Letters, 3: 1141-1146, 2003.
Randall, et al., "DNA Deformation in Electric Fields: DNA Driven Past a Cylindrical Obstruction", Macromolecules, 38: 2410-2418, 2005.
Randall, et al., "Electrophoretic Collision of a DNA Molecule with an Insulating Post", Physical Review Letters, 93: 058102-1-058102-4, 2004.

(Continued)

*Primary Examiner* — Krishnan S Menon
*Assistant Examiner* — Rebecca M Fritchman
(74) *Attorney, Agent, or Firm* — Sam Pasternack; MIT's Technology Licensing Office

(57) ABSTRACT

Apparatus and methods are described for achieving uniform stretching of polynucleotides in hybrid electrophoretic-gel, micro-constricting microfluidic channels. Polynucleotides in normally relaxed configurations are driven by an electric field along a microfluidic channel. The polynucleotides thread through a porous gel barrier formed in the channel and extend into a constriction where an electric field gradient exists. The combined action of the gel and field gradient acts to extend the polynucleotide configuration fully for direct linear analysis of the molecule.

22 Claims, 9 Drawing Sheets

OTHER PUBLICATIONS

Randall, et al., "Hook Formation of Electrically Driven DNA Collisions with Finite-Sized Obstacles", Mat. Res. Soc. Symp. 790: 3-8, 2004.

Randall, et al., "Methods to electrophoretically stretch DNA: microcontractions, gels, and hybrid gel-microcontraction devices", Lab Chip, 6: 516-525, 2006.

Riehn, et al., "Restriction mapping in nanofluidic devices", PNAS, 102: 10012-10016, 2005.

Tegenfeldt, et al., "The dynamics of genomic-length DNA molecules in 100-nm channels", PNAS, 101: 10979-10983, 2004.

Ueda, "Dynamics of long DNA confined by linear polymers", J. Biochem Biophys Meth, 41: 153-165, 1999.

Vreeland, et al., "Multiplexed, High-Throughput Genotyping by Single-Base Extension and End-Labeled Free-Solution Electrophoresis", Anal Chem, 74: 4328-4333, 2002.

\* cited by examiner

SYSTEM AND METHODS FOR STRETCHING POLYNUCLEOTIDES

RELATED U.S. APPLICATION DATA

The present application claims priority under 35 U.S.C. §119(e) to provisional application, U.S. Ser. No. 60/849,582 filed on Oct. 5, 2006, which is incorporated herein by reference.

GOVERNMENT SUPPORT

The work described herein was supported, in part, by a grant from the National Science Foundation (CAREER Grant No. CTS-0239012). The United States government may have certain rights in the invention.

FIELD OF THE INVENTION

This application for letters patent is generally directed to devices and methods useful for the analysis of polynucleotide molecules. In particular, the invention relates to the stretching of polynucleotides using a hybrid electrophoretic-gel/microconstricting fluidic device. Such a system allows for the linear analysis of polynucleotide molecules to provide polynucleotide sequence information.

BACKGROUND

Deoxyribonucleic acid (DNA) is a molecule present in all living organisms, and it contains information about the biological order of the organism to which it belongs. Each distinct living organism has a unique DNA structure, and the structure of the DNA largely determines the biological and physical make-up of each living organism. Knowing details about the structure of DNA molecules interests the scientific, medical, and criminal justice communities, because such detailed information can provide insight into biophysical functions, clues about ailments common to organisms and their cures, and the unique identity of one organism.

The DNA molecule has been well studied and is know to have the form of a double-helix strand comprising at least thousands of paired nucleotides spaced along the strand with a distance of about three nanometers between each pair. The paired nucleotides are present in the DNA in only four types, and are commonly identified by the letters A, C, G, and T. These four letters represent four molecules-adenine, cytosine, guanine, and thymine-belonging to a phosphate group which comprise the DNA. The specific order, or sequence, of these nucleotides along a DNA strand is frequently unknown, and is difficult to determine because of their shear number, submicroscopic size and spacing. Additionally, in a relaxed configuration the long DNA strand coils into a ball-like shape. It is the DNA sequence, also referred to as genetic code, that most interests the scientific, medical, and criminal justice communities.

SUMMARY

A need exists for a system useful for determining the base-pair sequence of polynucleotide molecules. In certain embodiments, the instrument and methods of the present invention enable the rapid sequencing of polynucleotides, including but not limited to DNA. In certain embodiments, a sequencing instrument would have a readily-manufacturable and low-cost element for extending long polynucleotides from a relaxed, coiled configuration to a substantially elongated and linear configuration. As a low-cost component, the polynucleotide linearizing element, or chip, could be a one-time-use, disposable component.

In various embodiments, a polynucleotide-linearizing microfluidic chip (PLMC), methods for its manufacture and methods for its use are described. The chip and methods can be employed to uncoil and elongate, or stretch, strands of polynucleotides such that they are presented for direct analysis as a substantially linear molecular chain. The direct analysis may include optical detection of fluorescing probes attached to a DNA strand.

By way of example, a PLC can be comprised of a patterned substrate bonded to a substantially flat substrate. The patterned substrate may contain at least one microfluidic channel disposed thereon. Either one, or both, of the substrates may have at least an optically transparent portion, so as to permit optical inspection of activity within the microfluidic channel. When bonded together, the flat substrate covers the fluidic channel forming a lumen. At least a portion of the channel is narrowed in a predefined manner, and a porous barrier is disposed across the channel at a location proximal to and upstream of the narrowed portion. The PLMC includes an opening for sample entry and an opening for sample exit at each end of the channel, so that a fluid containing a sample of polynucleotides may be introduced into the channel.

The sample entry portion of the device may comprise an entry reservoir fluidly coupled to the upstream end of the fluidic channel and having an opening allowing for the introduction of a fluid into the reservoir. The sample exit may comprise an exit reservoir for gathering polynucleotides and fluid that has traversed the length of the channel. The exit reservoir is fluidly coupled to the downstream end of the channel and may also have an opening allowing for the removal of air or fluid from the downstream end of the channel. The openings in the entry and exit reservoirs may also allow for introduction of electrical probes at both ends of the microfluidic channel. Such probes are useful in creating an electric field throughout the channel.

The microfluidic channel preferably extends along the surface of the patterned substrate, and may be comprised of several sections, as depicted in FIG. 1A. In various embodiments, these sections may comprise an entry section, a constricting section, a narrowed section, and an exit section. The depth of the channel sections into the patterned substrate may be less than about 10 microns. The width of the entry and exit sections may be less than about 500 microns, and their lengths each less than about 2 millimeters. The narrowed portion may be less than about 5 microns wide, and its length less than about 2 millimeters. The constricting section provides a tapering of channel's width, in a predefined manner, from the entry section's width to the narrowed section's width. The length of the constricting section may be less than about 100 microns. The channel's total length may be less than about 5 millimeters long. One or more microfluidic channels may be patterned on a single substrate.

By way of example, a polynucleotide-linearizing microfluidic chip can be manufactured from any suitable material such as, but not limited to, glass, plastic, polymer, inorganic material, ceramic, organic material, etc. In a method of fabrication, one or more microfluidic channels with entry and exit reservoirs can be patterned in a silicone substrate. In certain embodiments, the substrate used for the substrate is polydimethylsiloxane (PDMS). A flat fused silica glass substrate may be bonded to the patterned PDMS substrate by subjecting each substrate to a cleaning process and then placing them in contact. The surface energies of each provide sufficient bonding strength. After bonding, the reservoirs and fluidic channel can be filled with a photopatternable solution, e.g. a solution containing poly(ethylene glycol) constituents and an ultraviolet-sensitive photo-initiator. Exposing a portion of the photopatternable solution to an appropriate dose of ultraviolet (UV) radiation creates a porous semi-solid gel at the exposed area. The exposed area is located within the entry section of the channel, proximal to and upstream of the narrowed section of the channel, and forms a porous barrier across the channel or lumen. After exposure, a rinsing solution is used to remove substantially all photopatternable solution which has not been exposed to the UV radiation.

By way of example, a polynucleotide-linearizing microfluidic chip according to the embodiments herein can be used for direct linear analysis of polynucleotides to provide sequence information. A solution containing specimens of polynucleotides can be introduced into an entry reservoir on a microfluidic chip. The polynucleotides can optionally have fluorescent probes, or molecules, attached at targeted sites along the polynucleotide strand. After sufficient fluid fills the microfluidic channel and sufficient fluid enters or is added to the exit reservoir, electrodes can be introduced into the entry and exit reservoirs providing electrical contact with the fluid. An electrical potential difference can be applied across the electrodes, creating an electric field directed substantially along the microfluidic channel. The polynucleotide strands within the solution, predominantly in a coiled configuration, move under the influence of the electric field down the channel. The influence of the porous gel barrier and constricting section within the channel can promote elongation, or stretching, of the polynucleotides as shown, for example, in FIG. 9F. The stretching of such molecules, e.g. a length of DNA, is useful in analyzing the sequence of the polynucleotide.

After a substantially stead-state condition prevails, a region of the channel near the porous gel barrier and narrowed section can be illuminated with radiation selected to excite the fluorescent probes attached to the polynucleotides. This same region can be viewed with an optical microscope or optical imaging apparatus having filters to block the excitation radiation but pass the fluorescent radiation. As strands of polynucleotides move along the channel and interact with porous gel barrier and the constricting section, they uncoil and adopt extended configurations. In various embodiments, the extended configurations are substantially linear. As they pass within the irradiated region, the probes attached to the polynucleotides fluoresce and fluorescent intensity levels can be detected with the imaging apparatus. The distance between the fluorescing probes can be determined, and this information can be used to provide information about the polynucleotides specific structure.

In some embodiments, the polynucleotide may be DNA. The measured distance between fluorescing probes attached to the DNA, can provide information about the DNA's genetic code. Such information is useful to the scientific, medical, and criminal justice communities.

The foregoing and other aspects, embodiments, and features of the present teachings can be more fully understood from the following description in conjunction with the accompanying drawings. This application refers to various issued patents, published patent applications, journal articles, and other publications, all of which are incorporated herein by reference. If there is a conflict between any of the incorporated references and the instant specification, the specification shall control.

BRIEF DESCRIPTION OF THE FIGURES

The skilled artisan will understand that the drawings, described herein, are for illustration purposes only. In the drawings, like reference characters generally refer to like features, functionally similar, and/or structurally similar elements throughout the various figures. The drawings are not necessarily to scale, emphasis instead being placed upon illustrating the principles of the teachings. The drawings are not intended to limit the scope of the present teachings in any way.

Figure 8:
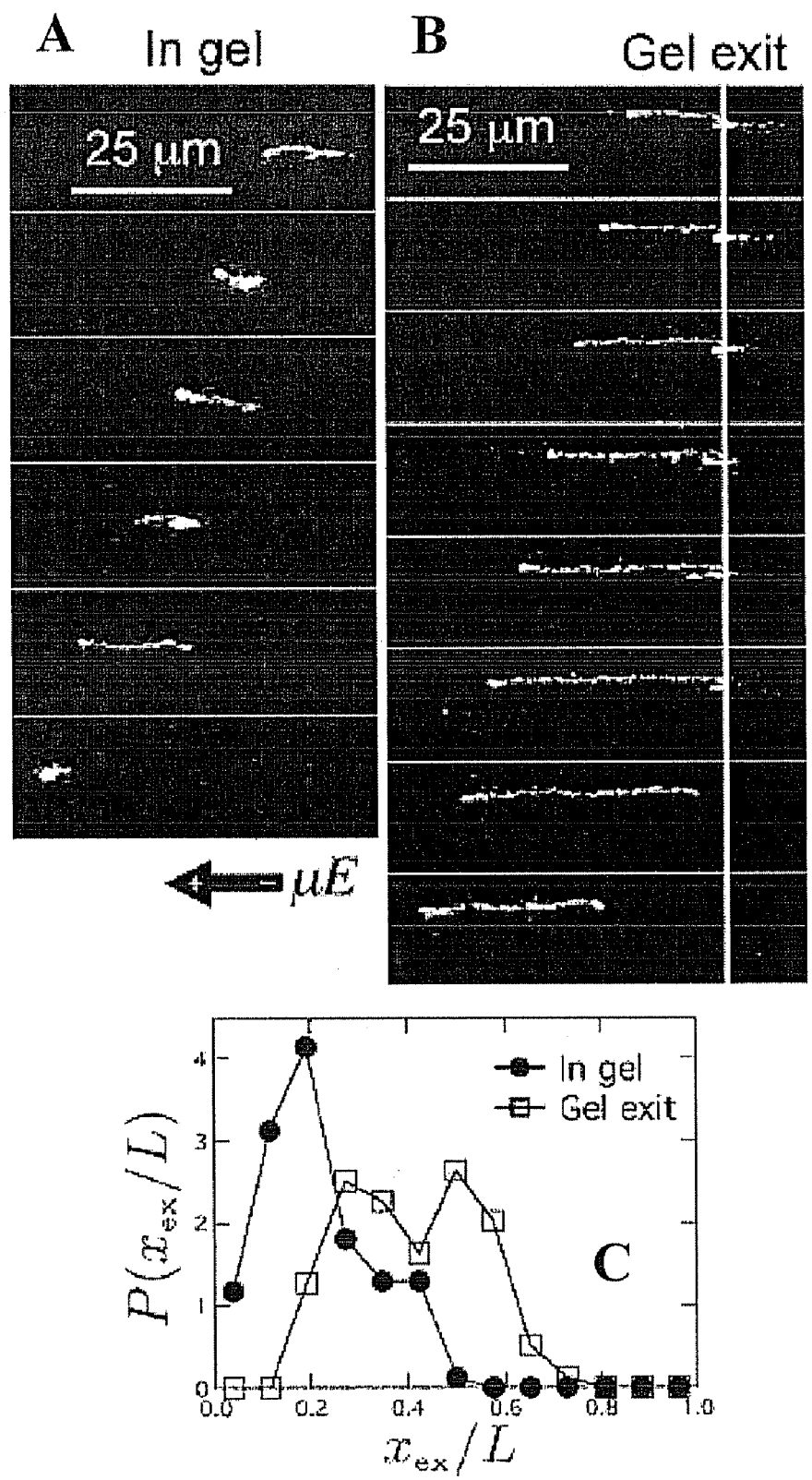

FIG. 8 depicts the behavior of two T4 DNA molecules reptating in UV cross-linked porous gel A, and exiting porous gel B within a straight-walled microfluidic channel having a uniform electric field directed along the channel. The vertical white line in B marks the end of the gel. The channel has dimensions of height=2 microns, width=200 microns, length=4.9 mm and E=10 V cm$^{-1}$. In A the images are spaced 6.7 s apart, and in B the images are spaced 0.6 s apart. Probability distributions (n=100 trials) of T4 DNA fractional extension x/L are plotted in C for the cases corresponding to A and B.

Figure 7:
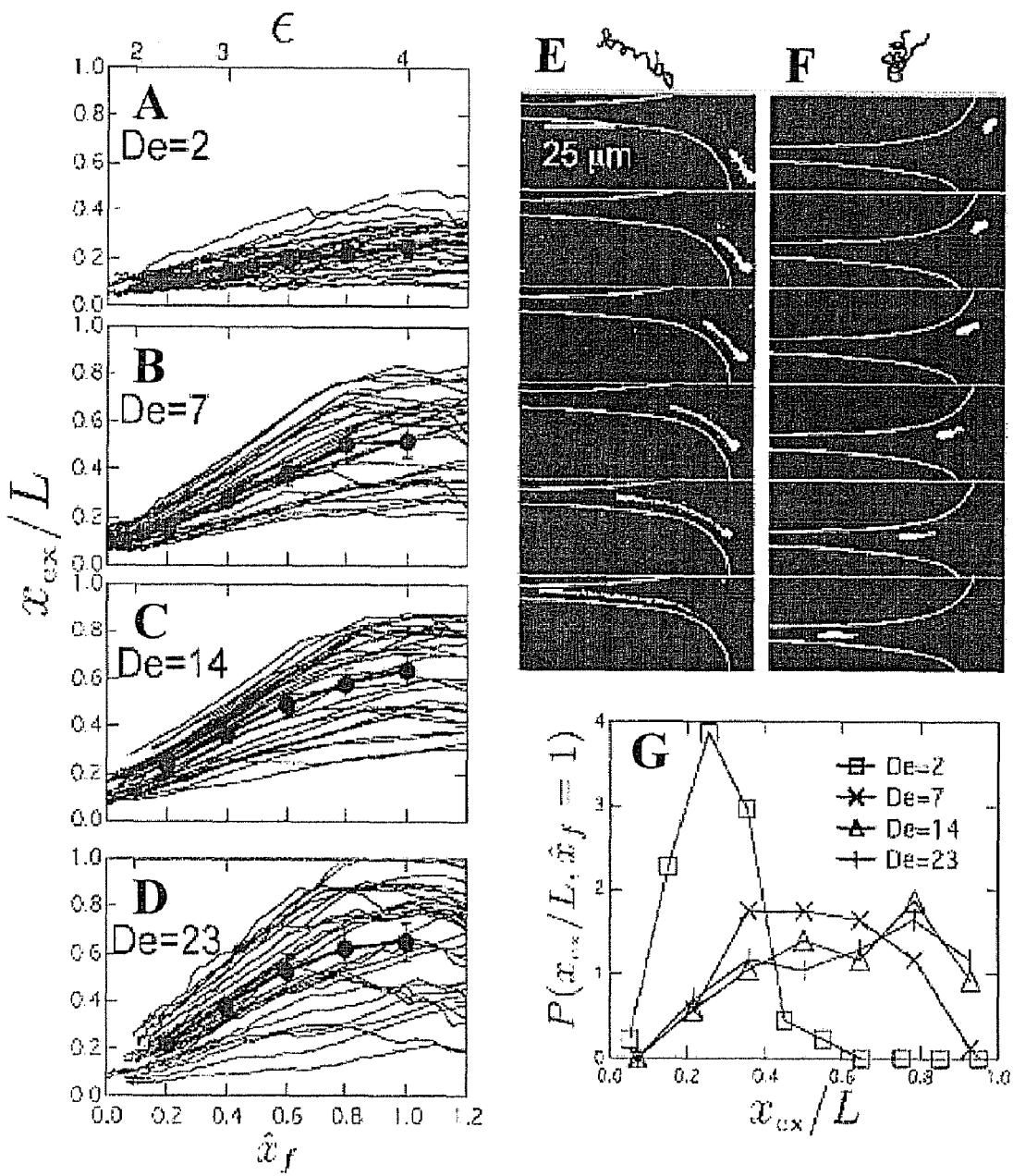
FIG. 7 contains plots of experimental data for DNA stretching trials carried out in a microfluidic channel having no porous barrier in which A-D represent fractional extension of T4 DNA in the constricting region at A De=2, B De=7, C De=14 and D De=23. For each plot in A-D 30 trials were recorded, and ensemble averages are given by solid circles. The sequential micrographs in E and F, separated by 0.17 s time steps between frames, are images of fluorescence from a labeled T4 DNA stretching in the constricting region at De=7 as it moves along the channel. The constricting section had hyperbolic geometry, and sidewalls are drawn in for reference. In E a dumbbell-shaped molecule in an initially open configuration enters the constricting region, and in F a folded molecule in an initially closed configuration enters the constricting region. For the case of F elongation is substantially less. The plots in G represent probability distributions (n=60 trials for each case), at each De studied, of T4 DNA fractional extension $x_{ex}/L$ as its front leaves the hyperbolic constriction.
Figure 9:
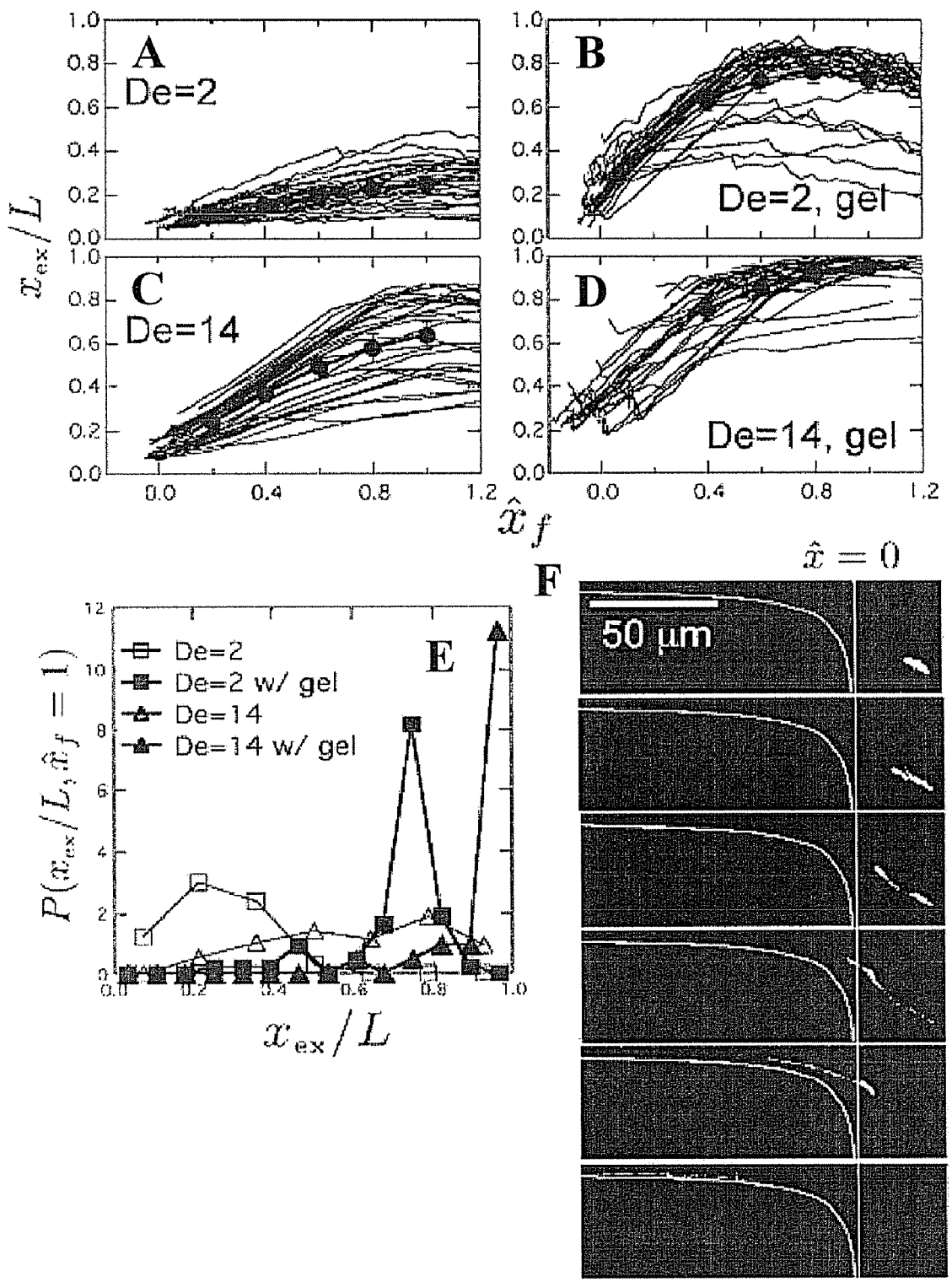

FIG. 9 compares the behavior of DNA stretching in a microfluidic channel without a porous barrier, as reported in FIG. 7, to the stretching behavior in a similar microfluidic channel having a porous gel barrier extending across the channel and located upstream and proximal to the constricting region. Plots A-D represent the fractional extension of T4 DNA within the constricting region at A De=2 and no gel barrier, B De=2 with a gel barrier, C De=14 and no gel barrier, and D De=14 with a gel barrier. The number of trials were n=30 for each case, and ensemble averages are plotted as solid circles. The plots in E compare the fractional extension probability distributions (n=60 trials) at $\hat{x}_f=1$ for cases with and without the porous gel in front of the constriction. The sequences of images in F shows the fluorescently labeled T4 DNA exiting the gel and entering the constricting region at De=14. A white line is drawn at the exit end of the gel barrier for reference. All frames are spaced by 0.67 s except the last two which are separated by 0.23 s.

Figure 10:
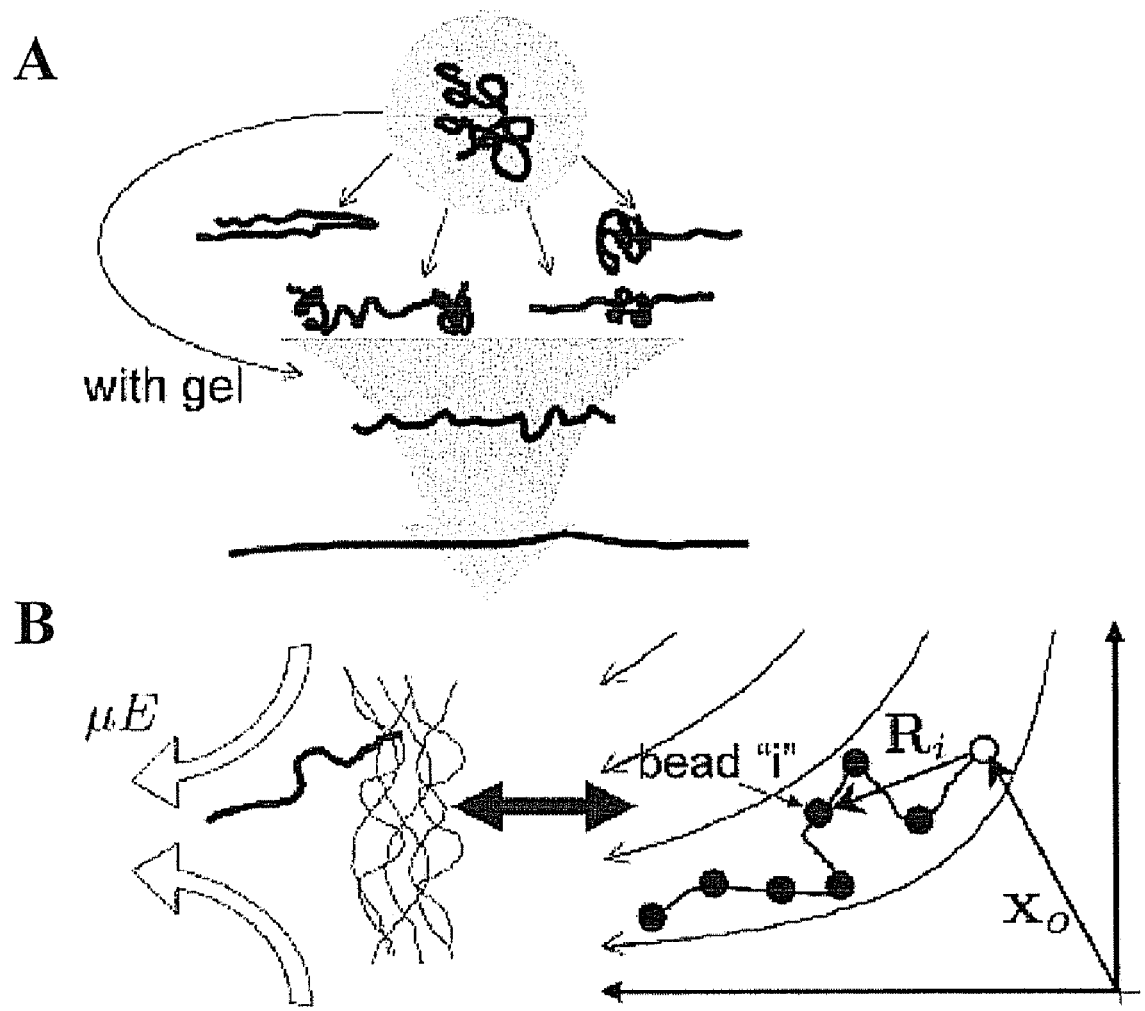

FIG. 10 is a collection of sketches illustrating the configuration manifold of a polymer coil transitioning to high extension. In A a coiled polymer, or molecular strand, in various configurations is transformed upon passing through a porous gel into an open, extended configuration. The sketch in B depicts a DNA molecule exiting a gel into an extensional field and a corresponding "pseudo-tethered" chain model that can be used to analyze the electrophoretic kinematic behavior of the molecule.

The features and advantages of the present invention will become more apparent from the detailed description set forth below when taken in conjunction with the drawings.

DETAILED DESCRIPTION OF CERTAIN EMBODIMENTS OF THE INVENTION

Figure 1A:
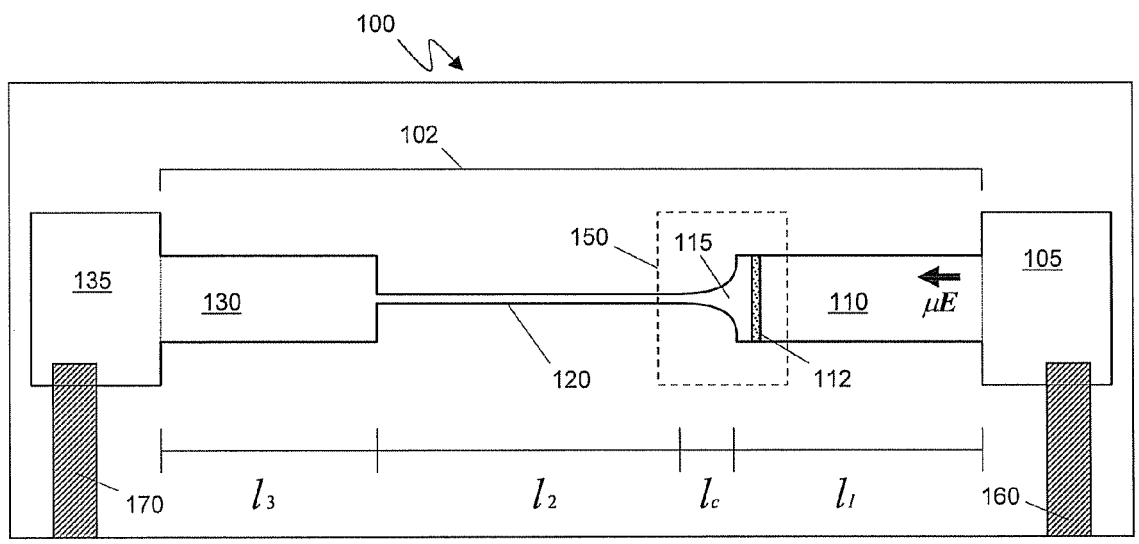
FIG. 1A is a plan view illustrating a portion of a polynucleotide-linearizing microfluidic chip (PLMC) according to one embodiment of the invention. A microfluidic channel having a constricting section $l_c$ extends along a length of the chip. The channel can be filled with a buffered solution, and a solution with polynucleotide specimens introduced into a sample entry reservoir 105 at the upstream end of the channel. The application of an electric field, directed substantially along the length of the channel, induces motion of electrically-charged polynucleotide strands down the channel, through a porous barrier 112, and through the constricting section.

In various embodiments, a polynucleotide-linearizing microfluidic chip (PLMC) is described. The PLMC comprises a substrate having defined thereon at least on microfluidic channel as depicted in FIG. 1A. A solution containing specimens of long polynucleotides, predominantly in relaxed, coiled configurations, may be introduced into the channel at an upstream end 105. The polynucleotides may be driven down the channel by the application of an electric field directed substantially along the length of the channel. When the coiled polynucleotides interact with a porous barrier 112 and constriction 115 within the channel, they can uncoil and adopt an extended configuration. In various embodiments, the extended configuration can be substantially linear. The PLMC is useful for enabling direct linear analysis of extended polynucleotides.

Referring now to FIG. 1A, a portion 100 of a PLMC having a microfluidic channel 102 according to an embodiment of the invention is depicted. The microfluidic channel may comprise several sections 110, 115, 120 and 130 each having lengths $l_1$, $l_c$, $l_2$, and $l_3$, respectively. At each end of the microfluidic channel there may be reservoirs 105 and 135 which provide means for conveying fluid into and out of the fluidic channel. At least one portion of the channel 115 is constricting, and located proximal to this constriction and just upstream is a porous gel barrier 112. The channel is covered with a flat substrate 220, FIG. 2, so that the structure forms a lumen. At least a portion of the channel in the vicinity of the constriction 115 is optically transparent, so that activity within the channel can be illuminated, viewed and recorded with optical imaging apparatus.

In detail, the length of the microfluidic channel 102 may be less than about 5 millimeters. In some embodiments, the channel length may be less than about 3 mm, and in other embodiments the channel length may be less than about 1 mm. The depth of the channel may be less than about 10 microns, and in some embodiments less than about 3 microns. The widths of the entry section 110 and exit section 130 may be less than about 500 microns in some embodiments, and less than about 200 microns in other embodiments. The narrowed section of the channel 120 may be less than about 5 microns in width, or less than about 2 microns in other embodiments. The walls of the channel 118, in FIG. 1B, at the constricting portion may follow a predefined curve, for example a hyperbolic curve of the form $$y = \frac{C}{x + \frac{2C}{w_1}} \quad (1)$$

where x and y are a set of coordinates with the origin lying on the symmetry line along the center of the channel at a point where the constriction begins and the inlet section ends. The length of the constricting region 115 may be less than about 200 microns in various embodiments, less than 100 microns in some embodiments and less than 50 microns in other embodiments. The length of the narrowed section 120 may be less than about 3 millimeters in some embodiments, and less than about 1 millimeter in other embodiments. In some embodiments, the narrowed section 120 may be omitted from the channel. In other embodiments, the narrowed section, the inlet section, and the outlet section each may be more than 3 millimeters in length.

One or more microfluidic channels and reservoirs may be patterned into the surface of a substrate made of polydimethylsiloxane (PDMS) using soft lithography techniques. (See, for example, Y. Xia and G. M. Whitesides, Angew. Chem., Int. Ed., 1998, vol. 37, p. 550.) An example of a constricting region of a microfluidic channel patterned into a PDMS substrate is shown in the scanning-electron micrograph of FIG. 4. The soft PDMS substrate may then be covered on its patterned side with a flat glass or plastic substrate to form lumens from the channels. The thickness of the glass substrate may be less than about 1 millimeter, and in some embodiments less than about 300 microns. In certain embodiments, the glass is low-fluorescence, ultraviolet-grade fused silica or crystalline quartz, so as to enable transmission of ultraviolet radiation used to excite fluorescent probes attached to the polynucleotides within the channel and to reduce undesirable fluorescence from the glass itself. The glass may also have deposited on one surface a dichroic anti-reflection coating which minimizes reflections at the glass/air interface of the excitation and fluorescent radiations. Cross-sectional views of the channel near the constricting region 115, identified in FIG. 1B by the dashed lines, may appear as illustrated in FIGS. 2A-2C. Preferably, the porous barrier 112 completely obstructs the lumen.

Figure 3:
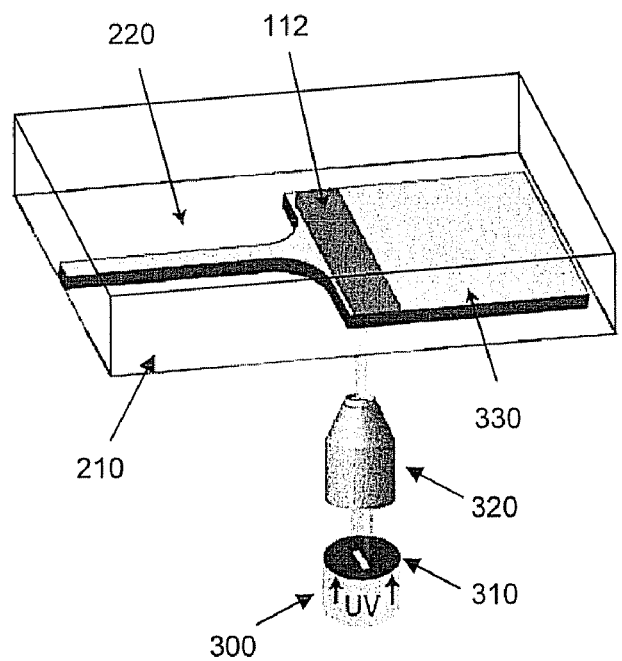
FIG. 3 is a perspective view illustrating the photopatterning of the porous barrier within the microchannel.

FIG. 3 depicts a method of forming the porous gel barrier within the lumen. In an embodiment of this approach, the fluidic channel 102 is filled with a solution 330 containing at least one polymer and a photoinitiator. An example of a solution useful for this approach is the following: 2.5% poly (ethylene glycol) 1000 dimethacrylate ("PEG-DM 1000", Polysciences, 15178), 2% poly(ethylene glycol) 400 diacrylate ("PEG-DA 400", Polysciences, 01871), 1% 2-hydroxy-2-methyl-propiophenone ("Darocur 1173", Aldrich, 405655) in 50% ethanol and 50% 56 TBE. The PEG-DM 1000 and PEG-DA 400 monomers crosslink when in the presence of the Darocur 1173 initiator and UV radiation. After filling the channel a portion near the constricting region is illuminated with UV radiation, for example at a wavelength of about 365 nm, which cross-links the polymers forming a porous gel 112 across the channel. The shape of the illuminated portion within the channel may be derived from photoreduction of a transparency mask 310 placed in the object plane of an objective lens 320 and flood illuminated with ultraviolet radiation 300. With this arrangement a demagnified image of the mask appears within the channel, which is located at the image plane of the lens 320. The demagnified image substantially defines the region of solution that will be transformed into a porous gel barrier 112. An exposure is carried out during which a sufficient dose of UV radiation is deposited within the channel to crosslink the polymers. After the UV exposure the channel is subjected to rinsing which removes the non-crosslinked polymer solution leaving the barrier in the channel.

In operation, the channel and reservoirs are filled with a buffered solution containing specimens of a polynucleotide, e.g., fluorescently-labeled DNA. In solution, a polynucleotide naturally carries a negative charge. Electrical probes are inserted into the reservoirs 105 and 135, and an electrical potential is applied across the probes. An electrical field develops within the channel and is directed along the length of the channel, pointing from left to right in FIG. 1A or from downstream to upstream. Since the polynucleotide carries a negative charge, the coiled molecules will move under the influence of the electric field from right to left, or from upstream to downstream. The viscosity of the buffered solution, amount of charge on the polynucleotide, and the magnitude of the applied electric field determine the mobility of the polynucleotide within the microfluidic channel. The coiled polynucleotides move along the channel until they encounter the porous gel barrier 112. At the barrier, the coils must open so that they can thread through small pores in the barrier. As a polynucleotide coil unravels and threads through the barrier, its downstream end extends into the constricting region 115. In this region the electric field condenses and its magnitude increases as the narrowed section of the channel is approached. The gradient in the electric field further acts to extend the polynucleotide strand, since the downstream end experiences a more forceful pull than the upstream end. The threading and pulling process continues until the polynucleotide strand emerges and releases from the gel barrier in a substantially linear configuration. An area of the channel in the vicinity of the constricting region may be illuminated with radiation selected to excite fluorescent probes attached to specific target sites along the polynucleotide strand, so that a fluorescent image of the extended polynucleotide may be obtained. An analysis of the location of fluorescent centers along the polynucleotide can reveal information about the sequence of molecules comprising the polynucleotide.

Various equivalent embodiments of the polynucleotide-linearizing microfluidic chip and methods pertaining thereto exist. For example, referring to FIG. 1A, the shape of the reservoirs 105, 135 at the ends of the channel may vary, e.g. square, round, elliptical, or may simply be longer extensions of the inlet 110 and outlet sections. The channels need not be straight, as shown in the figure, and may be curved or contain curved sections in some embodiments. The reservoirs may exist off-chip in some embodiments where capillary tubes may be inserted into a orifice fluidly connected to the inlet and outlet sections of the channel. The orifice may extend through the patterned substrate 210 or the cover substrate 220. In some embodiments the outlet section 130 may be omitted and the narrowed section 120 extend directly to the exit reservoir. In other embodiments, conductive electrodes 160, 170 may be patterned onto the patterned substrate 210 to enable electrical contact with fluid in the reservoirs. Additional traces may be patterned connecting the electrodes to large, conveniently-located contact pads at the periphery of the chip.

The curve of the walls 118 in the constricting region 115 may be altered in various equivalent embodiments. For example, in some embodiments the walls may follow a parabolic curve, or in other embodiments a circular curve. In other embodiments the walls may be linearly tapered from the inlet section 110 to the narrowed section 120.

There may be various materials used to fabricate the chip, including the use of various plastics and glasses, such as, but not limited to polystyrene, polymethylmethacralate, polyvinyl chloride, silicon, oxide-coated silicon, nylons, acrylic resins, polycarbonate, polyethelenes, and UV-curable adhesives, and sapphire. The patterned substrate may be formed by pouring a resin into a mold, or thermal embossing, or by various imprint lithography techniques. See for example, T. Bailey et al, *J. Vac. Sci. Technol. B,* 2000, vol. 18, p. 3572 and S. Y. Chou et al, *J. Vac. Sci. Technol. B,* 1996, vol. 14, p. 4129. In other embodiments, the channels may be formed by dry reactive-ion etching techniques, or in yet other embodiments, the channels may be formed by wet etching techniques. In some embodiments, the patterned substrate 210 may be formed from a hard material such as silicon or glass, and the cover 220 coated with a thin film of UV-curable adhesive before placing over the channels. After covering the channels, the cover and patterned substrate may be bonded by exposure to UV radiation. In some embodiments, the cross-sectional profile of the channels need not be rectangular in shape, and may have rounded corners or profiles.

More than one microfluidic channel as depicted in FIG. 1A may be patterned onto the substrate. For example, an array of channels having substantially identical characteristics may be defined on a single substrate, so that multiple trials can be made with the same substrate. In other embodiments, an array of channels having varying characteristics can be defined on a single substrate. For example, the shape of the constricting section and/or width of the narrowed section may vary from channel to channel, so that a particular geometry can be chosen for a particular molecule. In various embodiments, parameters of the porous barrier may be varied from channel to channel, for example changes in pore sizes, changes in location of the barrier, and/or changes in the extent of cross-linking of the barrier material.

In various embodiments, the porous barrier may be located at the boundary between the channel's inlet section 110 and constricting section 115, or the barrier may be located within the constricting section. The width and porosity of the barrier may be varied. In some embodiments the width of the barrier may be about 150 microns with pore sizes on the order of about one persistence length $l_p$ of the polynucleotide. In other embodiments, the barrier width may be greater than or less than about 150 microns, and pore sizes within the gel may be greater than or less than one persistence length $l_p$ of the polynucleotide. In some embodiments pore sizes may vary across the barrier. For example, pore sizes may be about one persistence length $l_p$ on the upstream side of the barrier and increase to multiple persistence lengths on the downstream side of the barrier. Such a graduation in pore size may be accomplished by making multiple exposures at varying UV dose of narrow lines extending across the channel, stepped sequentially along the channel, to define a barrier. Other materials may be used to form the barrier, such as photoresists which may be cross-linking types (such as novalak photoresists) or chain-scission types. An example of a chain-scission photoresist is polymethylmethacrylate (PMMA). In the case of a chain-scission resist, all areas of the fluidic channel would be exposed, except for the portion defining the barrier. The rinsing solution would then remove the exposed resist. In yet other embodiments, the barrier may be formed using techniques of nano-lithography, including the formation of a microfabricated array of nano-scale posts or obstacles. (S. W. P. Turner, M. Cabodi and H. G. Craighead, *Phys. Rev. Lett.*, 2002, 88, 128103.)

Theoretical Considerations

A more detailed understanding of the electrophoretic kinematics of polynucleotide molecules moving under the influence of the electric field and gel within the channel can be gained from theoretical considerations. For such an analysis the polynucleotides are taken to be large double-stranded molecules, typically of size 50-1000 thousand base pairs (kbp) and free of all in vivo proteins. For reference, this size of polynucleotide corresponds to about 0.01-1% of a typical human chromosome. The polynucleotide can be modeled as a polymer, and is primarily characterized by its persistence length $l_p$, contour length L, diffusivity D, and longest relaxation time $\tau$. The large polynucleotides considered here have $L \gg l_p$ so that they adopt coiled configurations (with radius of gyration $R_g$) at equilibrium in aqueous solvents. Backbone phosphate groups render DNA a uniformly negatively charged polymer at moderate pH. In the presence of a uniform electric field E, DNA coils move through solution at a size-independent velocity $\mu$E where $\mu$ is the electrophoretic mobility. (B. M. Olivera P. Baine and N. Davidson, *Biopolymers*, 1964, Vol. 2, 245.) In an electric field gradient, charged polymers can deform from their native coiled configurations. Using a bead-spring model (A. N. Gorban and I. V. Karlin, *Physica A*, 2004, 336, 391) of a polyelectrolyte in a low Debye length ($\kappa^{-1}$) solvent with $\kappa^{-1} \ll l_p$ it is found that deformation in electrophoretic fields characterized by $\mu$E is equivalent to deformation in hydrodynamic flows characterized by $u^\infty$ is equivalent (considering linear electrophoresis). Consequently, at low fields, the same kinematic approach can be used to study electrophoretic deformation as has been used in the past to study hydrodynamic deformation. Accordingly, the governing dimensionless group is the Deborah number De=$\dot{\epsilon}\tau$ where $\dot{\epsilon}$ is the electrophoretic strain rate (positive eigenvalue of $\mu\nabla$E) and $\tau$ is the longest relaxation time of the polymer. At a critical value of De=½, polymer deformation behavior transitions to strong extension in a homogeneous field. Ideal or "affine" deformation occurs when two material charges with mobility $\mu$ initially separated by a small distance $\delta$ move apart exponentially in this field, so that their distance apart at a later time is $\delta \cdot \exp(\epsilon)$, where $$\epsilon = \int \dot{\epsilon} \cdot dt \qquad (2)$$

is the accumulated electrophoretic strain. Polymers often do not stretch ideally due to their elasticity and conformation folds and kinks, so it is customary to compare the actual extension-strain of a polynucleotide ensemble in relation to the affine scaling.

The above analysis applies nicely at low external fields, however because electric and hydrodynamic forces and flows are intimately coupled, complex nonlinear electrophoretic effects may arise at field strengths on the order of kV cm$^{-1}$. These nonlinear electrophoretic effects arise when the double layer of the moving object becomes polarized. Polarization induces secondary fields and flows that affect the mobility, and also imposes a dielectrophoretic body force. (S. Dukhin *Adv. Colloid Interface Sci.*, 1993, Vol. 44, 1, N. A. Mishchuk and S. S. Dukhin, *Electrophoresis*, 2002, Vol. 23, 2012, M. Z. Bazant, K. Thornton and A. Ajdari, *Phys. Rev. E: Stat. Phys., Plasmas, Fluids, Relat. Interdiscip. Top.*, 2004, Vol. 70, 021506, T. M. Squires and M. Z. Bazant, *J. Fluid Mech.*, 2004, Vol. 509, 217.) Previous dielectrophoresis research has shown that DNA molecules do indeed polarize positively in AC fields, and can even exhibit polarization-induced aggregation both in high AC or DC fields. (C. L. Asbury and G. van den Engh, *Biophys. J.*, 1998, Vol. 74, 1024, C. L. Asbury, A. H. Diercks and G. van den Engh, *Electrophoresis*, 2002, Vol. 23, 2658, C.-F. Chou, J. O. Tegenfeldt, O. Bakajin, S. S. Chan, E. C. Cox, N. Darnton, T. Duke and R. H. Austin, *Biophys. J.*, 2002, Vol. 83, 2170, H. Isambert, A. Ajdari, J.-L. Viovy and J. Prost, *Phys. Rev. Lett.*, 1997, Vol. 78, 971, H. Isambert, A. Ajdari, J.-L. Viovy and J. Prost, *Phys. Rev. E: Stat. Phys., Plasmas, Fluids, Relat. Interdiscip. Top.*, 1997, Vol. 56, 5688, and S. Magnusdottir, H. Isambert, C. Heller and J.-L. Viovy, *Biopolymers*, 1999, 49, 385.) For the analyses used herein and for the experiments detailed in the examples below, field strengths and molecule sizes were used for which the dielectrophoretic force and other induced nonlinear effects were negligible. (G. C. Randall, Single Molecule Analysis of DNA Electrophoresis in Microdevices, PhD thesis, Massachusetts Institute of Technology, 2006.)

For the analysis, the downstream position of a molecule within the channel, the electrophoretic velocity, and the electrophoretic strain rate are normalized and expressed in non-dimensionalized quantities as:

$$\hat{x} = \frac{x}{l_c} \qquad (3)$$

$$\mu\hat{E} = \mu\frac{E}{E_i} \qquad (4)$$

$$\hat{\dot{\epsilon}} = \dot{\epsilon} \cdot \frac{l_c}{\mu E_i} \qquad (5)$$

where the origin for x is taken as the boundary between the inlet section 110 and constricting section 115, $l_c$ is the length of the constricting section, and $E_i$ is the magnitude of the uniform electric field in the inlet region of length $l_1$. The direction and magnitude of the electric field at any location within the channel can be determined using finite-element computer-solution techniques in which a simulation domain, representative of the particular geometry and electrical properties of materials within the domain, is divided into many sub-elements. Values for the electric field are determined within each sub-element by satisfying boundary conditions consistent with Maxwell's equations. Once the value of the electric field is known, values for the electrophoretic velocity and strain rate can be calculated.

An additional aspect of the analysis includes modeling the polynucleotide as a "bead-spring" polymer, as illustrated in the sketch of FIG. 10 (b). For the motion of the polynucleotide exiting the porous gel barrier, the molecule can be modeled as if it is semi-tethered at the gel. However, the polynucleotide is not necessarily stuck to the gel at its upstream end; the upstream end is simply moving at an average lower mobility. According to this model, the electrophoretic velocity $V_i$ at each "bead" of the polymer is given by $$\mu_i = (x_o + R_i) \cdot \nabla \mu E \quad (6)$$

where $R_i$ is the $i_{th}$ vector connecting the semi-tethered bead at $x_o$ to the $i_{th}$ bead.

The embodiments, methods and theoretical models set forth above can be better understood in view of the following examples. The examples are included as aids in describing the form and function of the invention, and should not be read as to limit the scope of the invention in any way.

EXAMPLES

Example 1

In this and the following examples, the electrophoretic kinematics of DNA molecules is investigated. In most examples, the microfluidic channel has a constricting section 115 with sidewalls 118 following a hyperbolic curve according to the expression given in EQ. 1. DNA are driven by an electric field to the hyperbolic constriction from the entry reservoir 105 and along the inlet section 110 of width $w_1$ and length $l_1$. The length of the constriction is $l_c$. After moving through the constriction 115, the DNA migrate down the narrowed section 120 of width $w_2$ and length $l_2$, and afterwards move though an abrupt expansion into the outlet section 130 of length $w_3$ and length $l_3$ and travel to the exit reservoir 135. The dimensions for the channel sections are: $w_1$=200 microns, $w_2$=3.8 microns, $w_3$=200 microns, $l_2$~1.5 mm, $l_2$=1.52 mm, $l_3$~1.5 mm, and $l_c$=80 microns. The hyperbolic constant C was 155 μm². (Note that $$C = w 2 l_c \div \left(2 - \frac{2w_2}{w_1}\right).)$$

Figure 5:
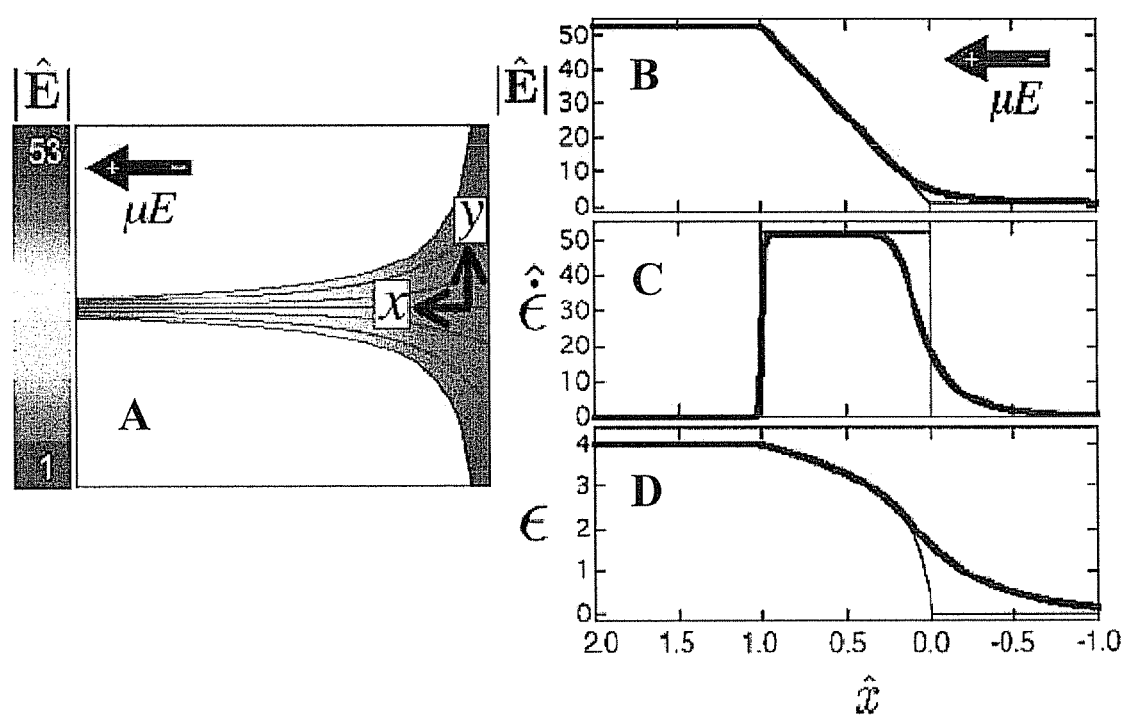
FIG. 5 contains computer-produced plots representing A the dimensionless electric field strength in the constricting section as determined from finite element calculations, B the dimensionless electric field strength along the y=0 trajectory within the microchannel, C the dimensionless strain rate along the y=0 trajectory, and D the accumulated strain along the y=0 trajectory. A hyperbolic constriction geometry was used for the finite element analysis in producing these plots. The thin lines in B-D correspond to an ideal hyperbolic contraction without abrupt entrance geometry or exit geometry effects.

A finite-element calculation was carried out for the above-described channel, and a 2-dimensional (2D) plot of the normalized electric field strength $|\hat{E}|$ in the hyperbolic section of the channel along with expected trajectories is shown in FIG. 5A. The molecules move from right to left and accelerate through the hyperbolic constriction to a maximum electrophoretic velocity in the narrowed section of the channel. FIG. 5B shows the normalized electric field strength in the vicinity of the constricting section for a trajectory along the y=0 trajectory, however other trajectories exhibit a similar trend. Since the electrophoretic velocity is directly proportional to field strength. FIG. 5B provides information about the electrophoretic velocity within the channel. Note that for this device the velocity is ~53 times greater in the narrowed section than at the inlet, and an approximately constant velocity gradient exists in the hyperbolic constriction.

FIG. 5C shows the normalized electrophoretic strain rate along the y=0 trajectory, and FIG. 5D is a plot of the accumulated strain along the same path. The corresponding values calculated for an idealized hyperbolic channel, i.e. one without any end effects such as an abrupt transition from a straight-walled channel to a hyperbolic channel, is indicated by the thin lines in FIGS. 5B-5D. The end effects that are more evident in FIGS. 5C-5D. Because of the abrupt change in channel geometry, the effects of electrophoretic-induced strain extend a full distance $l_c$ into the inlet section 110, before the physical constriction begins. Also, the varying strain rate persists about 25% into the constriction after which the strain rate remains substantially constant until about the last 5% of the constriction. The strain rate then abruptly falls to zero.

FIG. 5D shows the electrophoretic strain integrated along the y=0 trajectory:

$$\varepsilon = \int_{-\infty, y=0}^{\hat{x}, y=0} \frac{\hat{\dot{\varepsilon}} \cdot d\hat{x}}{|\mu \hat{E}|} \quad (7)$$

Note that the channel geometry in this example allows for a total strain of 4, however a significant strain ($\varepsilon \approx 2$) is achieved in the entrance region approaching the constriction. An effect of accumulated strain in the entrance region will be to reduce the effective strain experienced in the strong extensional region (De>½) when the maximum value of De is low. The accumulated strain at the entrance region can also slightly shift the DNA's configuration distribution at the hyperbolic inlet to slightly more extended states. (G. C. Randall and P. S. Doyle, *Macromolecules*, 2005, Vol. 38, 2410.) However, in the present example this shift is far less than the shift required to sufficiently avoid molecular individualistic effects, which are described below.

Example 2

Figure 4:
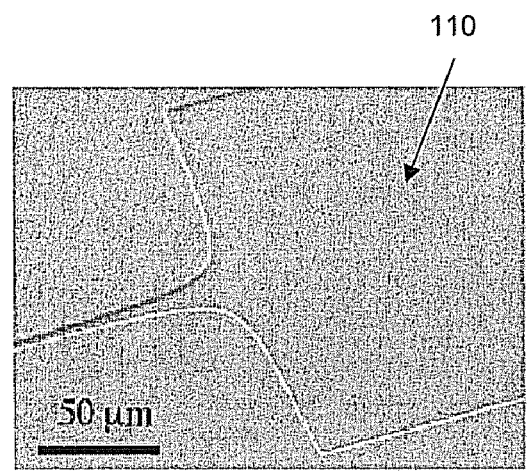
FIG. 4 is a scanning-electron-micrograph-produced perspective view of a portion of a patterned substrate where the entry section of the microfluidic channel meets the constricting section.

In this example, soft lithography was used to construct 2-micron high polydimethylsiloxane (PDMS) microchannels with geometry as described above in Example 1. (Xia and G. M. Whitesides, *Angew. Chem., Int. Ed.,* 1998, Vol. 37, 550.) A 10:1 PDMS crosslinking agent (Sylgard 184, Dow) was degassed for 60 minutes in vacuum at 15 inches Hg. The PDMS was then poured onto a silicon (Si) master substrate with the negative of the microchannel geometry patterned in AZ 5214 image reversal photoresist (Clariant) on the surface of the Si substrate. The silicon substrate was pretreated with a fluorinated silane monolayer (United Chemical Technologies) to prevent cured PDMS from sticking to the silicon master. After pouring, the PDMS was allowed to degas for about an hour in vacuum at 15 inches Hg. The PDMS was then cured at 65° C. for about 24 hours. Reservoirs measuring about 4 mm by 4 mm were cut at each end of the cured PDMS microchannel with a scalpel. A typical hyperbolic channel produced by this method is shown in FIG. 4.

Figure 1B:
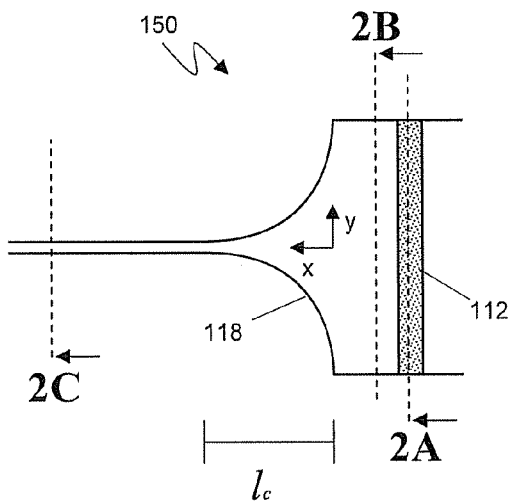
FIG. 1B is an enlarged plan view of an area of the channel, dashed box in FIG. 1A, containing the constricting section and porous barrier 112.
Figure 2A:
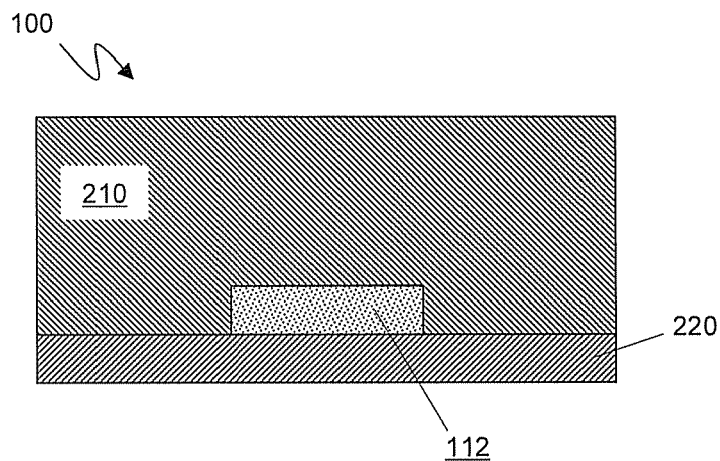
FIG. 2A-2C are cross-sectional views of portions of the microfluidic chip containing the channel at locations along the channel as designated in FIG. 1B.
Figure 2B:
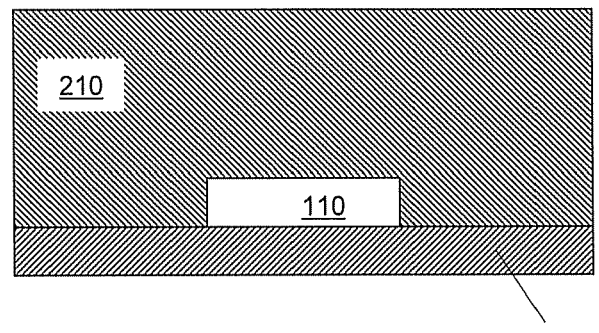
Figure 2C:
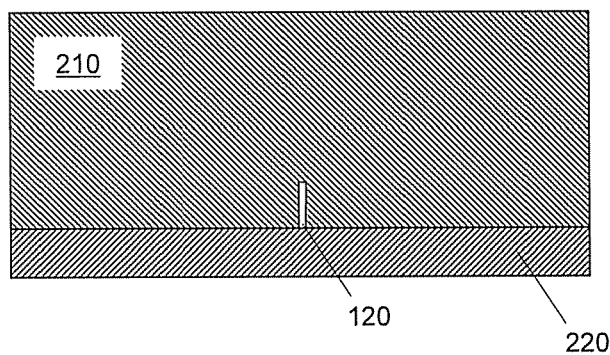

To form a porous barrier across the microfluidic channel, a photopatternable solution is selectively crosslinked, i.e. photopatterned, at a location proximal to and upstream of the hyperbolic constriction as indicated in FIGS. 1B and 3. The PDMS substrate is first soaked in an initiator solution of 10% 1-hydroxycyclohexyl phenyl ketone (Aldrich, 405612) in 70% ethanol and ultrapure water for 30 min. The PDMS substrate is then rinsed in ultrapure water, going through three cycles of rinsing in a water bath and then sonicating for 20 s. After rinsing, the PDMS is soaked in an ultrapure water bath for 30 min, and then carefully dry the PDMS and a cleaned glass slide. The glass slide is cleaned by soaking it in 1M NaOH for 15 minutes and rinsing in ultrapure water (MilliQ, Millipore). Both the PDMS and glass are treated in an RF plasma cleaner (Harrick, PDC-32G) for 5 s at 60 W, and then bonded together. Bonding results when the PDMS substrate and glass slide are joined after the plasma treatment. It is speculated that this manner of bonding is necessary when patterning gels within the formed microlumens, because otherwise the gel may swell in aqueous buffers and cause separation of the glass from the PDMS substrate.

The remaining photopatterning process is depicted in FIG. 3. (J. C. Love, D. B. Wolfe, H. O. Jacobs and G. M. Whitesides, *Langmuir,* 2001, 17, 6005.) After bonding the glass substrate to the PDMS substrate, the formed lumen is filled with 5 µL of a solution of 2.5% poly(ethylene glycol) 1000 dimethacrylate ("PEG-DM 1000", Polysciences, 15178), 2% poly(ethylene glycol) 400 diacrylate ("PEG-DA 400", Polysciences, 01871), 1% 2-hydroxy-2-methyl-propiophenone ("Darocur 1173", Aldrich, 405655) in 50% ethanol and 50% 5×TBE. The PEG-DM 1000 and PEG-DA 400 monomers crosslink when in the presence of the Darocur 1173 initiator and ultraviolet light. After the microfluidic channel is filled, the intended gel region is exposed with λ=365 nm UV radiation obtained from a microscope's illuminator. For this, a transparency mask (CAD/Art Services Inc., Bandon, Oreg.) is placed in the microscope's field stop aperture, and a UV excitation filter set (11000 v2: UV, Chroma, Rockingham, Vt.) is placed in the optical path between the illuminator and microfluidic channel. A 40×0.75 numerical aperture objective is used to produce a demagnified image of the transparency mask at the location of the microfluidic channel. The mask has an 8-mm-long by 2-mm-wide transparent region which creates a gel approximately 150 µm wide. The exposure is performed in two steps: a 3 s exposure, followed by a 10 s cooling time, and then a 2 s exposure. This two-step process is required to prevent the transparency mask from melting. Following exposure, the non-solidified solution is removed from the entry reservoir and then both reservoirs are filled with 0.5×TBE. The exit reservoir is overfilled and an electric potential of about 50 V is applied across the reservoirs to force a combined pressure-driven and electroosmotic rinsing flow from the outlet section to the inlet section of the microchannel for 30 min.

Example 3

Preparation and loading of the DNA into the fluidic channels can be carried out in many ways. In this example T4 DNA (169 kbp, L=70 µm, $R_g$~1.5 µm) are stained with a fluorescent dye (TOTO-1, 4.7:1 bp:dye molecule) and diluted in one of the following buffers: 5×TBE, 4% β-mercaptoethanol, and 0.1% polyvinylpyrrolidone (PVP, Polysciences, MW=10,000) (η=1 cP viscosity, pH=8.3) or 5×TBE, 4% β-mercaptoethanol, 0.1% PVP (Polysciences, MW=10,000), and 31% sucrose (η=6 cP, pH=7.9). The 6 cP buffer is used for a De=23 study to slow down electrophoretic dynamics to experimentally-observable speeds. The PVP is added to the formulation to dynamically coat the microchannel walls and minimize electroosmotic flow.

The measured electrophoretic mobility of the DNA has been found to be µ=−1.3±0.2 µm s$^{-1}$ V cm$^{-1}$ in the 1 cP buffer and µ=−0.17±0.02 µm s$^{-1}$ V cm$^{-1}$ in the 6 cP buffer. By convention, a minus sign is used for DNA mobility so that µE, which points in the direction of DNA motion, is in the opposite direction of E. Applying an electric field along the channel and tracking low-charged, surfactant-stabilized emulsion droplets ($R_{bead}$=0.25 µm, Ademtech, Pessac, France) in the 1 cP buffer solution enables the determination of the background electroosmotic mobility, which has been found to be $\mu_{EOF}$=0.15 µm s$^{-1}$ V cm$^{-1}$. The contour length of the DNA molecules has been found to be about 70 µm, and has been verified by consistent hyperbolic stretching experiments.

The mean square extension of 15 stretched T4 DNA molecules is measured as they dynamically relax in a 2 µm-thin PDMS microchannel, so that the longest relaxation time τ can be estimated for T4 DNA in the channels used for the present examples. The longest relaxation time is found to be about τ=1.7 s in the 1 cP buffer for the present examples. The DNA is fairly monodisperse, though some break during storage and handling. Approximately ⅔ of the DNA coils are intact T4 molecules, and broken molecules are generally easy to spot as they tend to be approximately half the size of an intact T4 molecule. Nevertheless, a possible source for error in the present examples is the quality of the DNA ensemble.

Example 4

The electric field within the vicinity of the constricting section can be characterized experimentally by performing bead electrophoresis within the channel. For this a 0.01% solution of carboxylated polystyrene fluorescent beads (negatively charged, $R_{bead}$=0.16 µm, Polysciences) was prepared in the 1 cP buffer along with an additional 0.5% tergitol (NP-10, J. T. Baker) to prevent beads from sticking to the channel walls. The bead solution was loaded into the entry reservoir 105 and an electric field was applied to drive the beads into the constriction. The maximum field strength at the constriction exit was $E_2$=425 V cm$^{-1}$, which is the near the highest field strength achieved in the DNA deformation studies reported in the examples. Nonlinear electrophoretic effects discussed above are negligible at these values of electric field. The center of mass position of 25 beads were tracked using optical imaging apparatus. Their trajectories, which are hyperbolic in shape under the influence of the electric field, are plotted in FIG. 6A.

Figure 6:
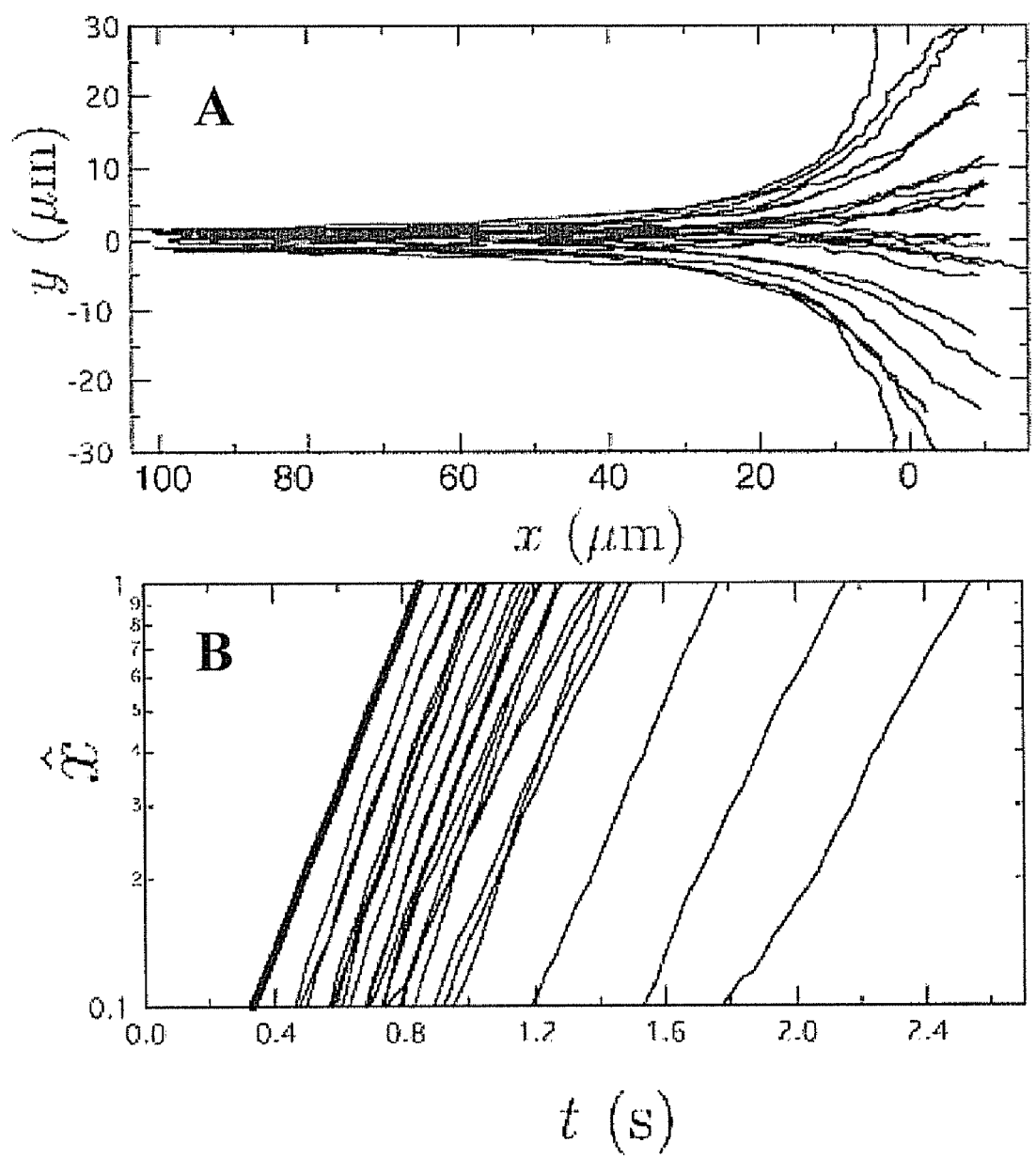
FIG. 6 contains plots of experimental data in which A represents trajectories of carboxylated bead electrophoresis with the constricting area of the channel for the experimental conditions ($E_2$=425 V cm$^{-1}$, $R_{bead}$=0.16 micron, fluid viscosity=1 cP). Plot B represents a semilog plot of the dimensionless position of a bead $\hat{x}$ as a function of time for the bead electrophoresis data shown in A. The thick line to the left is the affine scaling using $\dot{\epsilon}^{EL}$=4.4 s$^{-1}$.

A semi-log plot of the x-position of each bead as a function of time is shown in FIG. 6B. The thick line at left is the affine scaling x≈exp(ἐ·t), where ἐ=4.4 s$^{-1}$ in the homogeneous part of the extensional field. Each bead trace within the range 0.2<x̂(t)<0.9 is fitted to the expression $$\hat{x}(t)=\hat{x}(0)\exp(\dot{\epsilon}_{obs}\cdot t) \quad (8)$$

to determine the experimentally-observed electrophoretic strain rate $\dot{\epsilon}_{obs}$. The ensemble average strain rate was determined to be about $\langle\dot{\epsilon}_{obs}\rangle$=4.4±0.3 s$^{-1}$. An independent measurement of the velocity of beads in the narrow section 120 of the channel was made and then divided by the contraction length $l_c$ to obtain $\dot{\epsilon}_{obs}$=4.4±0.3 s$^{-1}$. Hence each bead accelerates affinely, as expected for this well-behaved field. In DNA experiments, the electrophoretic strain rate is determined using the latter method, i.e. by measuring the velocity of DNA molecules in the narrow section 120 of the device and computing $$\dot{\epsilon}\approx\frac{\mu E_2}{l_c}.$$

Example 5

For purposes of comparison, DNA stretching experiments were carried out in a microfluidic channel of the type described in Examples 1 and 2, but having no porous gel barrier. A typical experiment without a barrier 112 consisted of first soaking the PDMS substrate for about 12 h at about 45 C in 0.5×TBE to eliminate permeation driven flow. (G. C. Randall and P. S. Doyle, Proc. *Natl. Acad. Sci. U.S.A.,* 2005, Vol. 102, 10813.) Next, the microchannel was gently rinsed and dried, and a clean glass slide (soaked in 1 M NaOH for 15 min and rinsed in ultrapure water (MilliQ, Millipore)) was applied to the PDMS surface, having the microchannel defined thereon, forming a lumen of the channel. The channel was then filled with DNA solution, and an electric field applied across the reservoirs through platinum electrodes dipped into the reservoirs. After 15 minutes of equilibration, single DNA molecular dynamics were observed using an inverted fluorescence microscope (Axiovert 200, Zeiss) with a 63×, 1.4 NA objective and 100 W mercury lamp light source operating at 50% intensity (HBO 103, Zeiss). Images were captured at 30 frames per second with an EB-CCD camera (C7190-20, Hamamatsu) and NIH Image software. Digitized images had 8-bit pixel intensity values which ranged from 0-255.

The primary experimental observable is the extension of the DNA $x_{ex}$. For these examples, $x_{ex}$ is defined as the maximum linear dimension of the DNA's fluorescence cloud. (G. C. Randall and P. S. Doyle, *Macromolecules*, 2005, Vol. 38 2410.) For a stretched molecule, $x_{ex}$ is simply the distance between the front $(x_f, y_f)$ and back coordinates $(x_b, y_b)$. Adjustments for the effect of a curved contour length in the hyperbolic constriction are incorporated for any molecule that stretches over 40 µm long with a back coordinate $|y|>20$ µm. An equilibrium T4 coil in the inlet section of a 2 µm-deep channel was found to have a mean maximum linear dimension of about $(x_{ex})=4.6\pm0.8$ µm, or $(x_{ex}/L)\approx0.07$.

FIGS. 7A-D show the fractional extension $x_{ex}/L$ of T4 DNA driven through the constriction by electric fields at De=2, 7, 14, and 23. The fractional extension data is plotted against both the x-coordinate of the front of the DNA molecule $\hat{x}_f=x_f/l_c$ (lower axis) and the accumulated electrophoretic strain (top axis) calculated from FIG. 1D. The accumulated strain experienced by a DNA molecule is difficult to rigorously define since a stretched T4 molecule can span a large fraction of the contraction and even sample different strain rates in the entrance region. Recall that electrophoretic strain is a measure of how ideal charged objects move exponentially apart in a field gradient. Because the dynamics of how the front of the DNA moves away from its back is of interest, the strain experienced at the front coordinate of the molecule is chosen for plotting.

For the low value of De, it is found that the molecules do not extend appreciably before exiting the constricting region. None measured extend beyond half their total length. This is attributed to the inhomogeneous entrance region where $\hat{\epsilon}$ slowly ramps from 1 to 53. At De=2, the strong stretching criterion (De>½) is not achieved until $\hat{x}\approx0$. The accumulated 1.5 units of strain occurring before $\hat{x}\approx0$ cannot induce strong deformation, and decreases the strain experienced in the strong stretching regime to 2.5. The measured ensemble average $<x_{ex}/L>=0.26$ corresponds closely to results from homogeneous flow studies after $\epsilon\approx2.5$. (D. E. Smith and S. Chu, *Science*, 1998 vol. 281, p. 1335.) We conclude that these molecules do not experience enough strain in the strong stretching regime for any to achieve steady-state extensions.

At higher values of De, the strong stretching condition is met well before the constriction and the molecules experience $\epsilon\approx4$. This is ample strain for some molecules in the ensemble to reach steady state extension at the outlet, and the extension data more closely follows previously published results in flows, i.e. $<x_{ex}/L>=0.6$ at De=14 after $\epsilon\approx4$). (D. E. Smith and S. Chu, *Science*, 1998 Vol. 281, p. 1335.) It is noted that these extension results are achieved in a 2 µm-thin channel. This close agreement also implies that the entrance region and DNA finite size effects are not significantly altering the ensemble stretching dynamics.

In the experiments, a variety of extension behavior is observed, with some molecules extending much faster than others. This individualistic behavior is shown in FIG. 7E and FIG. 7F, which show individual DNA molecules stretching at De=7 from two particular configurations. FIG. 7E shows a T4 DNA molecule approaching the constriction in an open dumbbell-like configuration, and then significantly extending in the hyperbolic section. FIG. 7F shows a T4 DNA molecule that enters in a compact coiled configuration, and minimally extends in the constriction. (T. T. Perkins, D. E. Smith and S. Chu, *Science*, 1997, Vol. 276, 2016, and D. E. Smith and S. Chu, *Science*, 1998, Vol. 281, 1335,) This dissimilar behavior is a manifestation of "molecular individualism," in which the amount of extension of the DNA depends upon its configuration as it approaches the constriction. (T. T. Perkins, D. E. Smith and S. Chu, *Science*, 1997, Vol. 276, 2016, and P. G. de Gennes, *Science*, 1997, Vol. 276, 1999.) This sensitive dependence of stretching on the initial configuration makes stretching DNA uniformly at a moderate strain substantially impossible for the type of channel used in this example.

FIG. 7G shows plots of the fractional extension probability distributions for T4 DNA when the front of its fluorescence cloud exits the hyperbolic constriction, $\hat{x}_f=1$, at various values of De. Table 1 reports each ensemble's mean and standard deviation (rows 1-4). It is clear that as De increases, the distributions shift to higher extensions, but that improvements in extension are diminishing at higher values of De. These results indicate that in a finite-strain hyperbolic constriction, though some DNA may stretch near full contour length, other DNA will only minimally extend. This leads to a broad extension probability distribution, even at high values of De.

TABLE 1

| Deborah number: De | $<x_{ex}/L>$ at $\hat{x}_f = 1$ |
| --- | --- |
| 2 | 0.26 ± 0.10 |
| 7 | 0.54 ± 0.17 |
| 14 | 0.61 ± 0.21 |
| 23 | 0.60 ± 0.24 |
| 2, with gel barrier | 0.71 ± 0.13 |
| 14, with gel barrier | 0.95 ± 0.08 |

Example 6

For purposes of comparison, DNA stretching experiments were carried out in a microfluidic channel having uniformly straight sidewalls and filled with a porous gel. In this example, DNA deformation dynamics are studied in a 150-µm-wide, gel-filled, straight-walled channel subjected to a uniform electric field (E=10 V cm$^{-1}$, equivalent to the inlet field $E_i$ in the De=14 trials of Example 5).

The gel has pore sizes on the order of one persistence length $l_p$ which will force each molecule to adopt more extended configurations in order to reptate through the gel. FIG. 8A shows a time series of images of a T4 DNA moving through the gel. As it reptates through the gel, the DNA adopts extended so-called "I-shape" configurations. Though the DNA do adopt extended configurations while reptating in the gel, it was observed that they stretch even more upon exiting. In a uniform field, DNA stretching can result from a semi-tethering force exerted at the upstream end of the molecule. The stretching upon exit occurs because the average mobility of the molecule in the gel (at E=10 V cm$^{-1}$) is less than the mobility in free solution. However, the instantaneous mobility difference may vary significantly depending on the DNA's configuration. In an extreme example, some molecules act like they are tethered at the back due to formation of hairpin hooks around pieces of the gel. FIG. 8B shows an example of a T4 DNA exiting the gel in the uniform field, where the back end of the molecule becomes hooked on a piece of the gel and forms a hairpin. Many other exiting configurations are possible, e.g. dumbbells, half-dumbbells, or leading folds. (T. T. Perkins, D. E. Smith and S. Chu, *Science*, 1997, Vol. 276, 2016, and D. E. Smith and S. Chu, *Science*, 1998, Vol. 281, 1335.) FIG. 8C shows the fractional extension probability distribution of an ensemble of 100 T4 DNA molecules both inside the gel and as its back end exits the gel at $E=10\,V\,cm^{-1}$. Note that the configuration distribution has shifted to moderately extended states ($<x_{ex}/L>=0.21\pm0.11$) inside the gel as compared to ($<x_{ex}/L>=0.07\pm0.01$, as measured in a channel without the gel). Furthermore, the DNA stretch even more as they leave the gel ($<x_{ex}/L>=0.44\pm0.13$). Although the exiting DNA do not completely stretch, it may be possible to achieve greater stretching by increasing the field. However, the gel exit stretching distribution is still qualitatively broad, indicating that the details of an individual exiting DNA's configuration are still greatly influencing the stretching dynamics.

Example 7

DNA stretching experiments were carried out in an embodiment of the invention as set forth in Examples 1 and 2 above. In this example, a 150 µm-wide porous gel barrier was formed before the entrance to the hyperbolic constriction as indicated in FIG. 3. The downstream edge of the barrier was located at $\hat{x}=-0.13$. Following the rinsing step that substantially cleans the channel of residual photopatterning solution (see Example 2), the reservoirs are emptied and then filled with the DNA solution. A 15-minute equilibration period with an applied voltage of about 130 V across the reservoirs is maintained to load DNA and buffer into the microchannel and to allow for quenching of electroosmotic flow. The DNA observation and analysis then proceed as in Example 5.

FIGS. 9A-9D show a comparison of T4 DNA fractional extension without the gel and with the gel barrier at De=2 and 14. Note that for both De, the gel barrier causes a large majority of the ensemble to strongly stretch before exiting the hyperbolic constriction. This is seen more clearly in FIG. 9E which shows the fractional extensional probability distributions at $\hat{x}_f=1$. The very broad extension distributions observed without the gel, FIG. 7G, have transformed to narrow spikes for the hybrid channel having the gel barrier ($<x_{ex}/L>=0.71\pm0.13$ at De=2 and $<x_{ex}/L>=0.95\pm0.08$ at De=14). The stretching results at De=14 had particularly excellent uniformity, as 80% of the ensemble stretched over $x_{ex}/L=0.96$ and only 7% of the ensemble stretched less than $x_{ex}/L=0.80$. It was confirmed that the outliers corresponded to molecules having a leading fold in their configuration as they exited the gel. FIG. 9F shows a series of snapshots of a T4 molecule stretching as it exits the gel and enters the hyperbolic constriction at De=14.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. An apparatus for extending long molecules from a coiled configuration to an extended configuration comprising:
    a substrate;
    a fluidic channel defined on the substrate;
    a cover disposed on the substrate, covering at least a portion of the fluidic channel and forming a lumen;
    a sample entry portion;
    a sample exit portion;
    a constricting section defined within at least a portion of the fluidic channel;
    a porous barrier disposed proximally and upstream of the constricting section of the fluidic channel wherein pore sizes at an upstream side of the porous barrier are about equal to one persistence length of the molecules passing through the barrier, and wherein pore sizes increase to multiple persistence lengths at a downstream side of the porous barrier; and
    electrodes adapted to apply an electric field in a direction substantially along the length of the fluidic channel such that an electric field gradient is established within the constricting section,
    wherein the fluidic channel connects the sample entry portion to the sample exit portion.

2. The apparatus of claim 1 further comprising:
    a voltage source connected to the electrodes and adapted to provide a pre-selected amount of voltage across said electrodes.

3. The apparatus of claim 1 wherein the electrodes are thin wires dipped into the sample entry and sample exit portions, or the electrodes are thin metallic films deposited onto the surface of the substrate and onto walls defining the sample entry and sample exit portions.

4. The apparatus of claim 1 wherein walls of the channel defining the constricting section follow predefined curves, the curves being substantially symmetric with respect to the center of the channel, the shape of the curves selected from one of the following group:
    hyperbolic, parabolic, elliptical, and linear taper.

5. The apparatus of claim 4 wherein the width of the channel at the upstream end of the constricting section is greater than about 100 microns, the width of the channel at the downstream end of the constricting section is less that about 5 microns, the depth of the channel is less than about 5 microns, and the length of the constricting section is less than about 150 microns.

6. The apparatus of claim 1, the sample entry portion comprising:
    an entry reservoir fluidly coupled to an inlet section, the inlet section having substantially parallel walls and being greater than about 100 microns wide, less than about 5 microns deep, and having a length in a range between about 200 microns and about 20 millimeters; and the sample exit portion comprising an exit reservoir fluidly coupled to an outlet section, the outlet section having substantially parallel walls and being greater than about 100 microns wide, less than about 5 microns deep, and having a length in a range between about 200 microns and about 20 millimeters; wherein the inlet section is fluidly coupled to the constricting section, and the constricting section is fluidly coupled to the outlet section.

7. The apparatus of claim 6 further comprising:

a narrowed section defined within at least a portion of the channel, wherein the width of the narrowed section is substantially equivalent to the width of the constricting section at its downstream end, and the narrowed section is fluidly coupled to the constricting section.

8. The apparatus of claim 1 further comprising:

a narrowed section defined within at least a portion of the channel, the narrowed section fluidly coupled to the downstream end of the constricting section.

9. The apparatus of claim 1, the sample exit portion comprising:

an exit reservoir fluidly coupled to a narrowed section, the narrowed section having substantially parallel walls and having a width substantially equivalent to the downstream end of the constricting section, being less than about 5 microns deep, and having a length in a range between about 200 microns and about 20 millimeters; wherein the narrowed section is fluidly coupled to the constricting section.

10. The apparatus of claim 1 further comprising:

at least an optically transparent portion of the substrate or the cover disposed such that optical radiation may enter into or exit from at least a portion of the channel.

11. The apparatus of claim 10 further comprising:

an illumination source disposed to illuminate at least a portion of the fluidic channel; and high-resolution optical detection apparatus adapted to monitor radiation emitted from an area containing at least a portion of the fluidic channel, detect radiation within a pre-selected optical bandwidth, and record intensity levels of said detected radiation within said area.

12. The apparatus of claim 1 wherein the porous barrier substantially obstructs the lumen, and is located upstream of the constricting section within a distance which is about equivalent to the length of the constricting section.

13. The apparatus of claim 1 wherein the porous barrier substantially obstructs the lumen, and is located at about the entry of the constricting section, or is located within the constricting section.

14. The apparatus of claim 1 wherein the width of the porous barrier is less than about 200 microns.

15. The apparatus of claim 1 wherein the porous barrier comprises a gel formed from a photopatternable solution.

16. The apparatus of claim 15 wherein the photopatternahie solution contains a mixture of poly(ethylene glycol) 1000 dimethacrylate, poly(ethylene glycol) 400 diacrylate, and 2-hydroxy-2-methyl-propiophenone.

17. The apparatus of claim 15 wherein the photopatternable solution contains at least one form of a polymer selected from the following group: poly(ethylene glycol), linear polyacrylamide, cross-link polyacrylamide, polystyrene, polyacrylate, polymethacrylate, polyester, polyurethane, trimethylpropane triacrylate, 1,6-hexanediol diacrylate, tri(propyleneglycol) diacrylate and poly(methylmethacralate).

18. An apparatus for extending long molecules from a coiled configuration to an extended configuration comprising:

a constricting section defined within at least a portion of a microfluidic channel;

a porous barrier disposed proximally and upstream of the constricting section wherein pore sizes at an upstream side of the porous barrier are about equal to one persistence length of the molecules passing through the barrier, and wherein pore sizes increase to multiple persistence lengths at a downstream side of the porous barrier; and an electric field gradient within the constricting section of the microfluidic channel, wherein the porous harrier and electric field gradient cooperate in extending the long molecules.

19. The apparatus of claim 18, wherein the porous barrier substantially obstructs the microfluidic channel.

20. The apparatus of claim 18, wherein the porous barrier comprises a gel formed from a photopatternable solution.

21. The apparatus of claim 18, wherein the Deborah number within the constricting region obtains a value between about 2 and 23.

22. The apparatus of claim 18 further comprising an optically transparent portion of the microfluidic channel such that optical radiation may enter into or exit from the microfluidic channel.

* * * * *